United States Patent [19]

Broger et al.

[11] Patent Number: 5,142,063
[45] Date of Patent: * Aug. 25, 1992

[54] CHIRAL RHODIUM-DIPHOSPHINE COMPLEXES

[75] Inventors: Emil A. Broger, Magden; Yvo Crameri, Oberwil, both of Switzerland

[73] Assignee: Hoffmann-La Roche, Inc., Nutley, N.J.

[*] Notice: The portion of the term of this patent subsequent to Mar. 24, 2004 has been disclaimed.

[21] Appl. No.: 616,160

[22] Filed: Nov. 20, 1990

Related U.S. Application Data

[63] Continuation of Ser. No. 498,239, Mar. 22, 1990, abandoned, which is a continuation of Ser. No. 373,552, Jun. 30, 1989, abandoned, which is a continuation of Ser. No. 918,197, Oct. 14, 1986, abandoned.

[30] Foreign Application Priority Data

Oct. 18, 1985 [CH] Switzerland .......................... 4498/85

[51] Int. Cl.⁵ .................... C07B 53/00; B01J 31/24; C07F 15/00
[52] U.S. Cl. .................................. 548/402; 548/479; 549/292; 549/313; 549/319; 556/16; 556/21; 560/60; 560/179; 560/231; 562/470; 562/579; 562/606
[58] Field of Search ................ 548/402, 479; 556/16, 556/21; 562/470, 579, 606; 560/60, 179, 231; 549/292, 313, 319

[56] References Cited

U.S. PATENT DOCUMENTS

| | | | |
|---|---|---|---|
| 3,739,003 | 6/1973 | Codet et al. | 260/439 R |
| 3,794,671 | 2/1974 | Wilkinson | 260/429 R |
| 4,343,741 | 8/1982 | Townsend et al. | 548/412 |
| 4,539,411 | 9/1985 | Broger | 548/402 |
| 4,652,657 | 3/1987 | Broger | 548/402 |
| 4,879,389 | 11/1989 | Achiwa | 548/412 |

FOREIGN PATENT DOCUMENTS 1368431 9/1974 United Kingdom.

OTHER PUBLICATIONS

Nagy-Magos, Trans. Metal. Chem. 1, 215-219 (1976).
Knowles et al., "Studies of Asymmetric Homogeneous Catalysts", in Advances in Chemistry Series, 196, 1982, pp. 325-336.
Mitchell et al., J. Chem. Soc. (A), 3224-3230 (1971).
Uson et al., Chemical Abstracts 86:190183h.
Vastag et al., J. Mol. Catalysis 22:283 (1984).

Primary Examiner—Mark L. Berch
Attorney, Agent, or Firm—George M. Gould; William H. Epstein; Patricia S. Rocha

[57] ABSTRACT

The present invention describes novel chiral rhodium-diphosphine complexes having the formula $$[Rh(X)(Y)(Lp)]o$$

wherein X represents a residue of the formula X—COO⁻ in which Z signifies a group

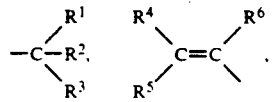

aryl or substituted aryl, wherein
$R^1$, $R^2$, $R^3$ = hydrogen, halogen, lower alkyl, aryl-lower alkyl, perfluoro-$C_{1-20}$-alkyl, aryl, substituted aryl, the group —$OR^7$, —$(CH_2)_m$—COA or AO-C—$(CF_2)_n$, with the proviso that at least one of $R^1$, $R^2$, and $R^3$ represents —$OR^7$, aryl or substituted aryl,
$R^4$, $R^5$, $R^6$ = hydrogen, halogen, lower alkyl, aryl-lower alkyl, perfluoro—$C_{1-20}$-alkyl, aryl, substituted aryl, —$(CH_2)_m$—COA or AOC—$(CF_2)_n$,
$R^7$ = hydrogen, lower alkyl, partially or completely halogenated lower alkyl, aryl, substituted aryl or aryl-lower alkyl,
A = The residue —OR or $NR'_2$,
R = hydrogen, lower alkyl, aryl, substituted aryl, aryl-lower alkyl or a cation,
R' = hydrogen, lower alkyl, aryl, substituted aryl or aryl-lower alkyl,
m = a number 0 to 20
n = a number 1 to 20,
Y = is a specific chiral diphosphine ligand,
L = is a neutral ligand selected from ethylene, propylene, cyclooctane, 1,5-hexadiene, norbornadiene, 1,5-cyclooxtadiene, acetonitrile and benzonitrile,
p = 0, 1 or 2, and
o = 1 or 2.

The invention also describes processes for manufacture of the above complexes. These complexes are used in asymmetric hydrogenations.

35 Claims, No Drawings

CHIRAL RHODIUM-DIPHOSPHINE COMPLEXES

This is a continuation of application Ser. No. 07/498,239 filed Mar. 22, 1990 now abandoned, which is a continuation of Ser. No. 07/373,552 filed Jun. 30, 1989, now abandoned, which is a continuation of Ser. No. 06/918,197 filed Oct. 14, 1986, now abandoned.

TECHNICAL FIELD

This invention relates to chiral rhodium-diphosphine complexes and to the use of such complexes for carrying out asymmetric hydrogenations.

BACKGROUND OF THE INVENTION

Chiral rhodium-diphosphine complexes and their use in asymmetric hydrogenations are already known from the literature. Usually, these complexes are cationic or contain—when they are neutral—chlorine, bromine or iodine as the ligand X. The optical yields which are obtained with the use of such complexes in asymmetric hydrogenations lie in the most favourable cases at about 80-84% in the case of the hydrogenation of ketopantolactone.

SUMMARY OF THE INVENTION

It has now surprisingly been found that, in comparison to the previously known complexes, the rhodium-diphosphine complexes of formula I in accordance with the invention are considerably more active and enantioselective, which means, in particular, that by employing them considerably smaller amounts of catalyst can be used, shorter reaction times are possible and optical yields of above 95% can be achieved.

The present invention is concerned with novel chiral rhodium-diphosphine complexes of the general formula

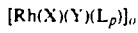

I.

where
p=0, 1 or 2 and o=1 or 2, and
wherein X, which can be optionally fixed to a carrier, represents a residue of the formula Z—COO⁻ in which Z signifies a group

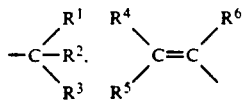

or aryl, wherein
$R^1$, $R^2$, $R^3$ = hydrogen, halogen, lower alkyl, aryl-lower alkyl, perfluoro-$C_{1-20}$-alkyl, aryl or the group —$OR^7$, —$(CH_2)_m$—COA or AOC—$(CF_2)_n$, with the proviso that at least one of $R^1$, $R^2$ and $R^3$ represents —$OR^7$ or aryl,
$R^4$, $R^5$, $R^6$ = hydrogen, halogen, lower alkyl, aryl-lower alkyl, perfluoro-$C_{1-20}$-alkyl, aryl or the group —$(CH_2)_m$—COA or AOC—$(CF_2)_n$,
$R^7$ = hydrogen, lower alkyl, partially or completely halogenated lower alkyl, aryl or aryl-lower alkyl,
A = the residue —OR or —$NR'_2$,
R = hydrogen, lower alkyl, aryl, aryl-lower alkyl or a cation,
R' = hydrogen, lower alkyl, aryl or aryl-lower alkyl,
m = a number 0 to 20 and
n = a number 1 to 20, and wherein
Y represents a chiral diphosphine ligand and
L represents a neutral ligand,
with the exception of those complexes of formula I in which X, which can be optionally fixed to a carrier, represents a residue of the formula ⁻Z—COO in which Z signifies the group

perfluorophenyl, perfluorobiphenyl or a residue of the formula

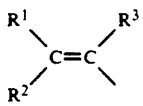

and $R^1$, $R^2$ and $R^3$ represent halogen, lower alkyl, perfluorophenyl, perfluoro-$C_{1-20}$-alkyl, hydrogen or the group —COA or AOC—$(CF_2)_n$— in which A signifies the residue —OR or —$NR'_2$, with the proviso that at least one of the substituents $R^1$, $R^2$ and $R^3$ signifies fluorine, R signifies hydrogen, lower alkyl or a cation, R' signifies hydrogen or lower alkyl and n signifies a number 1 to 20.

The invention is also concerned with the manufacture of the rhodium-diphosphine complexes of formula I and with their use for asymmetric hydrogenations.

DESCRIPTION OF THE INVENTION

The term "lower alkyl" signifies in the scope of the present invention straight-chain or branched alkyl groups with 1 to 9 carbon atoms as e.g. methyl, ethyl, propyl, isopropyl, n-butyl, isobutyl, tert.butyl, pentyl, hexyl, heptyl, octyl or nonyl and the like. The term "halogen" signifies fluorine, chlorine, bromine and iodine, with fluorine being preferred. The term "perfluoro-$C_{1-20}$-alkyl" signifies in the scope of the present invention not only straight-chain, but also branched chains which may also be optically active, whereby not all of the hydrogen atoms need be replaced by fluorine atoms. When not all of the hydrogen atoms are replaced by fluorine atoms, then, in particular, a terminal hydrogen atom is frequently present. Insofar as X is fixed to a carrier, this is effected via a group —COA.

The term "aryl" used in connection with the compounds of formula I signifies in the scope of the present invention not only aromatic hydrocarbons, but also aromatic heterocycles with 4 to 14 carbon atoms. Oxygen and nitrogen come into consideration, in particular, as the hetero atoms. Furthermore, the rings can be not only unsubstituted, but also substituted, in which case halogen, hydroxy, lower alkyl, perfluoro-lower alkyl, lower alkoxy and formyl preferably come into consideration as substituents. Moreover, an aryl group present can be complexed to a transition metal such as chromium, iron or also nickel.

The term "aryl" used hereinafter in connection with the compounds of formula II signifies in the scope of the present invention phenyl which can optionally have in the para- and/or meta-position lower alkyl or lower alkoxy groups, preferably methyl or methoxy groups, or di-lower alkylamino groups, preferably dimethylamino groups, as well as a carboxy, carbamoyl, cyano or lower alkoxycarbonyl group. Moreover, two aryl groups on the same phosphorus atom can be attached directly to each other via the o-position or also via a methylene, ethylene or propylene group. The term "aryloxy" signifies groups in which the aryl residue has the previous significance.

The term "lower alkoxy" signifies groups in which the alkyl residue has the previous significance. Furthermore, the notation "▼" signifies that the corresponding residue is situated above the plane of the molecule, while the notation "≡" signifies that the corresponding residue is situated below the plane of the molecule. The symbol n signifies a number of 0 to 20, preferably of 1 to 12, especially of 1 to 8.

The term "neutral ligand" signifies in the scope of the present invention a readily exchangeable ligand such as an olefin, e.g. ethylene, propylene, cyclooctene, 1,5-hexadiene, norbornadiene, 1,5-cyclooctadiene and the like, a nitrile such as acetonitrile and benzonitrile or also the solvent which is used, etc. This ligand can be exchanged in the hydrogenation. Where more than one such ligand is present, these can also be different from one another.

As used herein, the term "carrier" is defined to mean inorganic or organic support materials, e.g. Merrifield type polymers, containing suitable functional groups e.g. $-CH_2Cl$, $-CH_2OH$, $-CH_2NH_2$ and the like, for the attachment of a group $-COA$.

As chiral diphosphine ligands there can be used in principle any diphosphine ligands which are known in connection with asymmetric hydrogenations and which optionally can also be fixed to a carrier. Such ligands are known and are readily accessible to a person skilled in the art. For example, ligands which come into consideration in the scope of the present invention are known from: Marko, L. et al., Aspects of Homogenous Catalysis, 4, 145-202 (1981); Japanese Patent Application No. 67411 of 4.6.1978, (Derwent 8180 C); German Offenlegungsschrift No. 2 161 200; European Patent Publication No. 104 375. Especially suitable and preferred ligands are e.g. the chiral phosphines of the general formula

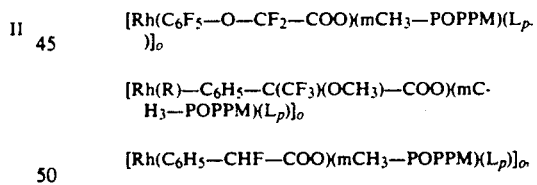

II wherein $R^8$ represents aryl and $R^9$ represents the group $-CO-R^{10}$, $-SO_2-R^{10}$, $-PO(R^{10})_2$ or $-PS(R^{10})_2$ in which $R^{10}$ signifies aryl, lower alkyl, di-arylamino, di-lower alkylamino, aryloxy or lower alkoxy.

Preferred rhodium-diphosphine complexes of formula I are those in which Z represents the group

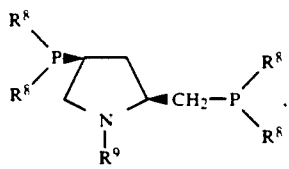

and one of the substituents $R^1$, $R^2$ and $R^3$ signifies the residue $-OR^7$ and the other two signify fluorine, hydrogen, perfluoro-$C_{1-20}$-alkyl or aryl, as well as those in which one of the substituents $R^1$, $R^2$ and $R^3$ represents aryl and the other two represent fluorine, hydrogen or perfluoro-$C_{1-20}$-alkyl, with the proviso that at least one of them signifies fluorine. Where the ligand X is chiral, this can be present in racemic form or preferably in optically active form.

Preferred diphosphine ligands of formula II are those in which $R^8$ represents phenyl, p-tolyl, m-tolyl or 3,5-xylyl and $R^{10}$ in the residues $R^9$ signifies phenyl, p-tolyl, m-tolyl, p-lower alkoxycarbonylphenyl or tert.butoxy. Especially preferred phosphines are, moreover, those in which the residue $R^9$ represents the group $-PO(R^{10})_2$. The following can be named as examples of preferred diphosphine ligands:

(2S,4S)-4-(Di-m-tolylphosphino)-2-[(di-m-tolylphosphino)methyl]-1-(diphenylphosphinoyl)-pyrrolidine (mCH$_3$-POPPM);

(2S,4S)-4-(diphenylphosphino)-2-[(diphenylphosphino)methyl]-1-(diphenylphosphinoyl)-pyrrolidine; (POPPM);

(2S,4S)-4-(di-p-tolylphosphino)-2-[(di-p-tolylphosphino)methyl]-1-(diphenylphosphinoyl)pyrrolidine; (pCH$_3$-POPPM);

(2S,4S)-4-(diphenylphosphino)-2-[(diphenylphosphino)methyl]-1-(di-p-carbomethoxyphenylphosphinoyl)-pyrrolidine;

(2S,4S)-4-(diphenylphosphino)-2-[(diphenylphosphino)methyl]-1-(tert.butoxycarbonyl)-pyrrolidine (BPPM);

(2S,4S)-4-(di-m-tolylphosphino)-2-[(di-m-tolylphosphino)methyl]-1-(tert.butoxycarbonyl)-pyrrolidine (mCH$_3$-BPPM).

Especially preferred rhodium-diphosphine complexes of formula I are those in which one of the substituents $R^1$, $R^2$ and $R^3$ signifies the residue $-OR^7$ and the other two signify fluorine or one signifies trifluoromethyl and the other signifies phenyl, as well as those in which one of the substituents $R^1$, $R^2$ and $R^3$ represents phenyl and the other two represent fluorine or one signifies hydrogen and the other signifies fluorine and the diphosphine ligand is mCH$_3$-POPPM. The complexes of the formulae:

[Rh(C$_6$F$_5$—O—CF$_2$—COO)(mCH$_3$—POPPM)(L$_p$)]$_o$

[Rh(R)—C$_6$H$_5$—C(CF$_3$)(OCH$_3$)—COO)(mCH$_3$—POPPM)(L$_p$)]$_o$

[Rh(C$_6$H$_5$—CHF—COO)(mCH$_3$—POPPM)(L$_p$)]$_o$, where p=0, 1 or 2 and o=1 or 2, are particularly preferred.

The rhodium-diphosphine complexes of formula I in accordance with the invention can be manufactured in a manner known per se. They can be manufactured, for example, by a) reacting a rhodium complex of the formula

[RH(X)(L$_n$)]$_m$    III.

wherein X and L have the above significance, n=1, 2, 3 or 4 and m=1 or 2,
with chiral diphosphine ligand, or b) reacting a rhodium complex of the formula

[RH(L$_{n+1}$)]$^+$A$^-$    IV, wherein L and n have the above significance and A⁻ represents an anion, especially $BF_4^-$, $ClO_4^-$, $PF_6^-$ or $B(C_6H_5)_4^-$, with a chiral diphosphine ligand and a salt containing the anion X, or c) reacting a rhodium-diphosphine complex of the formula $$[Rh(L_p)(Y)]^+ A^- \qquad V.$$

wherein L, Y and A⁻ have the above significance and p represents a number of 1 to 3,
with a salt containing the anion X, or d) reacting a chiral rhodium-diphosphine complex of the formula $$[Rh(X^1)(L_n)(Y)] \qquad VI.$$

wherein $X^1$ signifies halogen, n = 1 or 2 and L and Y have the above significance,
with a silver salt or thallium salt of the formula $$Ag-X \text{ or } Tl-X \qquad VII.$$

wherein X has the above significance.

The reactions of the rhodium complexes of formulae III, IV, V and VI in accordance with reaction variants a)-d) can be carried out in a manner known per se. This is conveniently carried out in an inert organic solvent. As examples of such solvents there can be named: aromatic hydrocarbons such as benzene, toluene etc, esters such as ethyl acetate etc, cyclic ethers such as tetrahydrofuran or dioxan, lower alcohols such as methanol, ethanol and the like or also mixtures thereof. The reaction can be effected at temperatures between about 0° C. to about 100° C., preferably at about 15° C. to about 60° C., but with the strict exclusion of oxygen.

The term "salt containing the anion X" signifies in the scope of the present invention especially ammonium salts, alkali metal salts, alkaline earth metal salts as well as other suitable metal salts. Such salts are known substances. In order to increase the solubility of such salts in certain solvents, a suitable crown ether can be added if desired.

The rhodium-diphosphine complexes of formula I are catalysts of precursors thereof. Since their true chemical structure can not be given with certainty, they are also characterized in that they are obtainable by reacting a rhodium complex of formula III-VI in accordance with reactions a) to d) mentioned previously.

The rhodium complexes of formulae III, IV, V and VI which are used as starting materials are known substances or analogues of known substances which can be prepared readily in analogy to the known substances.

As already mentioned, the rhodium-diphosphine complexes of formula I in accordance with the invention are useful as catalysts in asymmetric hydrogenations. They are of particular interest in connection with the asymmetric hydrogenation of α,β-unsaturated acids and esters as well as of a-keto-carboxylic acids and esters and of a-keto-lactones. In particular, they are of interest for the asymmetric hydrogenation of dihydro-4,4-dimethyl-2,3-furandione (ketopantolactone) to the corresponding R-(a-hydroxy-β,β-dimethyl-q-butyrolactone) [R-(−)-pantolactone].

In order to carry out the aforementioned asymmetric hydrogenations, the complexes of formula I can be added as such to a solution of an asymmetric compound to be hydrogenated. Alternatively, they can also be formed in situ in the presence of an asymmetric compound to be hydrogenated.

The asymmetric hydrogenations can be carried out in suitable organic solvents which are inert under the reaction conditions. As such solvents there can be named, in particular, lower alkanols such as e.g. methanol or ethanol, aromatic hydrocarbons such as benzene or toluene, cyclic ethers such as tetrahydrofuran or dioxan, esters such as e.g. ethyl acetate or also mixtures thereof and the like. The ratio between rhodium and the ligand Y conveniently lies between about 0.05 and about 5 mol, preferably between about 0.5 and about 2 mol, of rhodium per mol of ligand. The ratio between rhodium and the residue X conveniently lies between about 0.01 and about 20, preferably between about 0.5 and about 10 mol of rhodium per mol of residue X. The ratio between rhodium, in the complexes of formula I, and the compounds to be hydrogenated conveniently lies between about 0.00001 and about 5 wt. %, preferably between about 0.0001 and about 0.01 wt. %.

The asymmetric hydrogenations using the complexes of formula I can be carried out conveniently at temperatures of about 0° C. to about 100° C., preferably of about 20° C. to about 70° C. These hydrogenations are conveniently effected under pressure, especially under a pressure of about 1 to 100 bar, preferably 2 to 50 bar.

EXAMPLES

The following Examples serve to illustrate the invention and are in no way a limitation thereof.

In these Examples of abbreviations have the following significance:

COD = 1,5-cyclooctadiene
BPPM; mCH₃-POPPM: diphosphines mentioned on pages 6 and 7.

The enantiomeric composition (enantiomeric excess e.e.) was determined by gas-chromatographic determination of (R)- and (S)-pantolactone on a 25 m capillary column with chiral phase (SP-300). In several cases the optical rotations of (R)-(−)-pantolactone were also measured at 589 nm (D-line), at 20° C. and a concentration of 3% in deionized water. The values for the optical purities are based on $[a]_D^{20} = -51.6°$ (c = 3, H₂O) for purest (R(-)−)-pantolactone.

EXAMPLE 1

254.2 mg (0.389 mmol) of a 40% aqueous tertrabutyl-ammonium hydroxide solution, 108.2 mg (0.389 mmol) of perfluorophenoxyacetic acid, 157.8 mg (0.389 mmol) of bis-(1,5-cyclooctadiene)-rhodium(I) tetrafluoroborate and 281.7 mg (0.389 mmol) of 2S,4S)-4-(di-m-tolyphosphino)-2-8(di-m-tolyphosphino)methyl]-1-(diphenylphosphinoyl)-pyrrolidine (mCH₃-POPPM) were suspended in 50 ml of toluene in a 100 ml glass flask in a glove box (O₂ content < 1 ppm). The suspension was subsequently stirred at 22°-25° C. for 16 hours, whereby an orange-red, almost clear catalyst solution formed.

EXAMPLE 2

A 500 ml autoclave was charged in a glove box (O₂-content < 1 ppm) with 40 g (0.31 mol) of ketopantolactone, 160 ml of toluene and 50 ml of catalyst solution prepared according to Example 1. The hydrogenation was carried out at 40° C., at a constant pressure of 40 bar of H₂ and while stirring intensively. After 1 hour the conversion was 99.8%. After a total hydrogenation time of 4 hours the yellow hydrogenation solution was flushed from the autoclave and the autoclave was subsequently rinsed three times with 50 ml of toluene each time. The combined toluene solutions were evaporated on a rotary evaporator at 60° C./17 mbar. The residue (42 g) was distilled at 130°-150° C. (bath temperature) and 12 mbar. There were obtained 40.3 g (99.3%) of (R)-a-hydroxy-$\beta$, $\beta$ -dimethyl-q-butyrolactone [(R)-(−)-pantolactone] with an optical purity of 92.8% e.e.

EXAMPLES 3-29

A catalyst solution was prepared in a manner analogous to Example 1 and the hydrogenation of ketopantolactone was subsequently carried out analogously to Example 2. The results are compiled in the following Table.

| Example No. | [Rh (X)(Y)(L)][1)] X | Y | Solvent | Pressure [bar] | % Conversion after 1 hour | (R)-(−)-Pantolactone e.e. % | Remarks |
|---|---|---|---|---|---|---|---|
| 3 | phenyl-CHCOO(OH) [S] | m-CH₃POPPM | Toluene | 40 | 99.3 | 90.6 | |
| 4 | phenyl-CHCOO(OCH₃) [R] | m-CH₃POPPM | " | 40 | 99.6 | 91.2 | 2) |
| 5 | furyl-CHCOO(OH) [R, S] | m-CH₃POPPM | " | 40 | 99.4 | 87.9 | |
| 6 a | pentafluorophenyl-CH₂COO | m-CH₃POPPM | " | 40 | 99.8 | 91.8 | |
| b | | BPPM | " | 40 | 95.2 | 89.2 | |
| 7 | 3-CF₃-phenyl-CH₂COO | m-CH₃POPPM | " | 40 | 96.1 | 90.4 | |
| 8 | 2-OH-phenyl-CH₂COO | m-CH₃POPPM | " | 40 | 99.9 | 92.0 | |
| 9 | furyl-C(O)COO | m-CH₃POPPM | " | 40 | 99.6 | 89.7 | |
| 10 | phenyl-CHCOO(CH₂COOH) [R, S] | m-CH₃POPPM | Toluene | 40 | 92.5 | 90.0 | 3) |
| 11 a | phenyl-CHCOO(F) [R, S] | m-CH₃POPPM | " | 40 | 99.7 | 94.6 | |
| b | | BPPM | " | 40 | 98.4 | 88.5 | |
| 12 | furyl-COO | m-CH₃POPPM | " | 40 | 99.7 | 90.0 | |

-continued

| Example No. | [Rh (X)(Y)(L)][1] X | Y | Solvent | Pressure [bar] | % Conversion after 1 hour | (R)-(−)-Panto- lactone e.e. % | Remarks |
|---|---|---|---|---|---|---|---|
| 13 | 2-OH, 1-COO benzene | m-CH₃POPPM | " | 40 | 59.5 | 89.9 | 4) |
| 14 | 2,6-(OH)₂, 1-COO benzene | m-CH₃POPPM | " | 40 | 99.6 | 92.4 | |
| 15 | 1-naphthyl-COO | m-CH₃POPPM | " | 40 | 96.2 | 87.9 | |
| 16 | 9-anthracenyl-COO | m-CH₃POPPM | " | 40 | 99.5 | 91.2 | |
| 17 | (CO)₃Cr-C₆H₅-COO | m-CH₃POPPM | " | 40 | 99.6 | 90.0 | |
| 18 | C₆H₅-OCH₂COO | m-CH₃POPPM | Toluene | 12 | 99.9 | 94.8 | |
| 19 | C₆F₅-OCH₂COO | m-CH₃POPPM | " | 12 | 98.4 | 92.3 | |
| | | | | 40 | 99.7 | 92.5 | |
| 20 | C₆Cl₅-OCH₂COO | m-CH₃POPPM | " | 12 | 99.4 | 94.1 | |
| | | | | 40 | 99.9 | 94.8 | |
| 21 | CH₃OCH₂COO | m-CH₃POPPM | " | 40 | 99.2 | 92.5 | 5) |
| 22 | C₂H₅OCH₂COO | m-CH₃POPPM | " | 40 | 99.1 | 90.0 | |
| 23 | C₆H₅-C(CF₃)(OCH₃)-COO | | | | | | 6) |
| a | [R] | m-CH₃POPPM | " | 12 | 99.1 | 95.6 | |
| b | | m-CH₃POPPM | Ethyl acetate | 12 | 77.1 | 94.8 | |
| c | | m-CH₃POPPM | THF | 12 | 73.1 | 94.0 | |
| d | | BPPM | Toluene | 40 | 56.5 | 92.2 | |
| 24 | [S] | m-CH₃POPPM | Toluene | 12 | 98.2 | 92.5 | 7) |
| 25 | 1-naphthyl-O-CH₂COO | m-CH₃POPPM | " | 40 | 100.0 | 89.9 | |

-continued

| Example No | [Rh (X)(Y)(L)][1] X | Y | Solvent | Pressure [bar] | % Conversion after 1 hour | (R)-(−)-Panto-lactone e.e. % | Remarks |
|---|---|---|---|---|---|---|---|
| 26 | CHO, —OCH₂COO (phenyl) | m-CH₃POPPM | Toluene | 40 | 98.7 | 93.0 | |
| 27 | —OCHCOO [R,S] / CH₃ (phenyl) | m-CH₃POPPM | " | 40 | 99.6 | 90.7 | |
| 28 | (CH₃O)₂CHCOO | m-CH₃POPPM | " | 40 | 97.8 | 90.5 | |
| 29 a | F F F F F, —OCF₂COO | m-CH₃POPPM | " | 12 | 68.5 | 92.6 | 8) |
| b | | BPPM | " | 40 | 99.9 | 92.5 | |

[1] L = 1,5-Cyclooctadiene
[2] [α]$_D^{20}$ = −47.2° (c = 3, H₂O), opt. purity 91.4%
[3] [α]$_D^{20}$ = −46.24° (c = 3, H₂O), opt. purity 89.6%
[4] [α]$_D^{20}$ = −45.93° (c = 3, H₂O), opt. purity 89.0%
[5] [α]$_D^{20}$ = −47.8° (c = 3, H₂O), opt. purity 92.6%
[6] [α]$_D^{20}$ = −48.7° (c = 3, H₂O), opt. purity 94.4%
[7] S/Rh = 15 720 (weight ratio ketopantolactone to rhodium metal)
[8] S/Rh = 62 880 (weight ratio ketopantolactone to rhodium metal)

EXAMPLE 30

A 500 ml steel autoclave was charged in a glove box (O₂ content <1 ppm) with 30 g (0.104 mol) of isopropyl a-oxo-q-(1,3-dioxo-2-isoindolyl)-butyrate, 110 ml of toluene and a catalyst solution prepared analogously to Example 1 from 165 g (0.292 mmol) of a 40% tetrabutyl-ammonium hydroxide solution, 68.3 mg (0.292 mmol) of (S)-a-methoxy-a-trifluoromethylphenylacetic acid, 118.4 mg (0.292 mmol) of bis-(1,5-cyclooctadiene)-rhodium (I) tetrafluoroborate and 164.7 mg (0.292 mmol) of (2S, 4S)-1-tert.butoxycarbonyl-4-diphenylphosphino-2-diphenylphosphinomethyl-pyrrolidine.

The hydrogenation was effected at a constant pressure of 10 bar of H₂, at 40° C. and while stirring intensively for 24 hours. The hydrogenation solution was evaporated, the residue was chromatogrpahed on silica gel and the fractions containing the product were evaporated. There were obtained 29.5 g (97.4%) of isopropyl (R)-a-hydroxy-q-(1,3-dioxo-2-isoindolyl)-butyrate as pale yellow crystals. M.p. 78°–82° C. Enantiomeric purity 78.5% (in accordance with GC determination on a 21 m capillary column [Se 54] as the camphanic acid ester). [α]$_D^{20}$ = −4.4° (c−1, CH₃OH); optical purity 79.0%.

What is claimed is:

1. A chiral rhodium-diphosphine complex of formula $$[Rh\ (X)\ (Y)\ (L_p)]_o \qquad I,$$

wherein p=0, 1 or 2 and o=1 or 2, and wherein X represents a residue of the formula Z—COO⁻ in which Z signifies a group

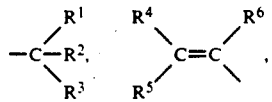

aryl or substituted aryl, wherein

R¹, R², R³=hydrogen, halogen, lower alkyl, aryl-lower alkyl, perfluoro-C₁₋₂₀-alkyl, aryl, substituted aryl, the group —OR⁷, —(CH₂)$_m$—COA or AO-C—(CF₂)$_n$, with the proviso that at least one of R¹, R² and R³ represent —OR⁷, aryl or substituted aryl, R⁴, R⁵, R⁶=hydrogen, halogen, lower alkyl, aryl-lower alkyl, perfluoro-C₁₋₂₀-alkyl, aryl, substituted aryl, —(CH₂)$_m$—COA or AOC—(CF₂)$_n$, R⁷=hydrogen, lower alkyl, partially or completely halogenated lower alkyl, aryl, substituted aryl or aryl-lower alkyl, A=the residue —OR or NR′₂, R=hydrogen, lower alkyl, aryl, substituted aryl, aryl-lower alkyl or a cation, R′=hydrogen, lower alkyl, aryl, substituted aryl or aryl-lower alkyl, m=a number 0 to 20 n=a number 1 to 20,

Y=

(2S,4S)-4-(Di-m-tolyphosphino)-2-[(di-m-tolylphosphino)methyl[-1-(diphenylphosphinoyl)-pyrrolidine;

(2S,4S)-4(diphenylphosphino)-2-[(diphenylphosphino)-methyl]-1(diphenylphosphinoyl)-pyrrolidine;

(2S, 4S)-4-(di-p-tolylphosphino)-2-[(di-p-tolylphosphino)methyl]-1-diphenylphosphinoyl)pyrrolidine;

(2S, 4S)-4-(diphenylphosphino)-2[(diphenylphosphino)methyl]-1-(di-p-carbomethoxyphenylphosphinoyl)-pyrrolidine;

(2S, 4S)-4-(diphenylphosphino)-2[(diphenylphosphino)methyl]-1-(tert.butoxycarbonyl)-pyrrolidine;

(2S, 4S)-4-(di-m-tolylphosphino)-2-[(di-m-tolyphosphino)methyl]-1-(tert.butoxycarbonyl)-pyrrolidine; and L = represents a neutral ligand selected from the group consisting of ethylene, propylene, cyclooctane, 1,5-hexadiene, norbornadiene, 1,5-cyclooctadiene, acetonitrile and benzonitrile with the provision that complexes of formula I above do not include those complexes in which X, represents a residue of the formula Z—COO⁻ wherein Z signifies the group

perfluorophenyl, perfluorobiphenyl or a residue of the formula

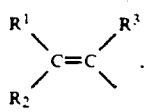

and $R^1$, $R^2$ and $R^3$ represent halogen, lower alkyl, perfluorophenyl, perfluoro-$C_{1-20}$-alkyl, hydrogen, -13 COA or AOC—$(CF_2)_n$—, in which A signifies the residue —OR or —NR'$_2$, with the proviso that at least one of the substituents $R^1$, $R^2$ and $R^3$ signifies fluorine, R signifies hydrogen, lower alkyl or a cation, R' signifies hydrogen or lower alkyl and n signifies a number 1 to 20.

2. The chiral complex of claim 1 wherein Z represents the group

and $R^1$, $R^2$ and $R^3$ have the definitions given in claim 1.

3. The chiral complex of claim 1 wherein one of the substituents $R^1$, $R^2$ and $R^3$ is —$OR^7$ and the other two substituents are independently selected from fluorine, hydrogen, perfluoro-$C_{1-20}$-alkyl, aryl or substituted aryl and $R^7$ has the definition given in claim 1.

4. The chiral complex of claim 1 wherein one of the substituents $R^1$, $R^2$ and $R^3$ represents phenyl and the other two are independently selected from fluorine, hydrogen, and perfluoro-$C_{1-20}$-alkyl, with the proviso that at least one of them signifies fluorine.

5. The chiral rhodium-diphosphine complex of claim 1 wherein
X is

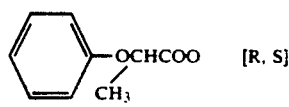

Y is (2S,4S)-4-(Di-m-tolylphosphino)-2-[(di-m-tolylphosphino)methyl]-1-(diphenylphosphinoyl)pyrrolidine, and L is 1,5-Cyclooctadiene.

6. The chiral rhodium-diphosphine complex of claim 1 wherein

X is

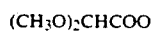

(CH₃O)₂CHCOO

Y is (2S,4S)-4-(Di-m-tolylphosphino)-2-[(di-m-tolylphosphino)methyl]-1-(diphenylphosphinoyl)pyrrolidine, and L is 1,5-Cyclooctadiene.

7. The chiral rhodium-diphosphine complex of claim 1 wherein
X is

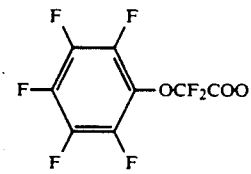

Y is (2S,4S)-4-(Di-m-tolylphosphino)-2-[(di-m-tolylphosphino)methyl]-1-(diphenylphosphinoyl)pyrrolidine or (2S,4S)-4-(diphenylphosphino)-2-[(diphenylphosphino)methyl]-1-(tert.butoxycarbonyl)-pyrrolidine, and L is 1,5-Cyclooctadiene.

8. The chiral rhodium-diphosphine complex of claim 1 wherein
X is

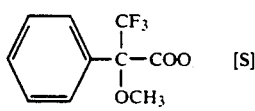

Y is (2S,4S)-4-(Di-m-tolylphosphino)-2-[(di-m-tolylphosphino)methyl]-1-(diphenylphosphinoyl)pyrrolidine, and L is 1,5-Cyclooctadiene.

9. The chiral rhodium-diphosphine complex of claim 1 wherein
X is

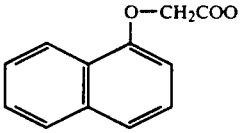

Y is (2S,4S)-4-(Di-m-tolylphosphino)-2-[(di-m-tolylphosphino)methyl]-1-(diphenylphosphinoyl)pyrrolidine, and L is 1,5-Cyclooctadiene.

10. In the process of asymmetric catalytic hydrogenation of α,β-unsaturated acids and esters, α-keto-carboxylic acids and esters, and α-keto-lactones, the improvement comprising substituting the catalyst used in said hydrogenation with the chiral rhodiumdiphosphine complex of claim 1.

11. The chiral rhodium-diphosphine complex of claim 1 wherein
X is

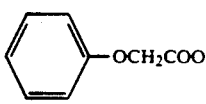

Y is (2S,4S)-4-(Di-m-tolylphosphino)-2-[(di-m-tolyl-phosphino)methyl]-1-(diphenylphosphinoyl)pyr-rolidine, and L is 1,5-Cyclooctadiene.

12. The chiral rhodium-diphosphine complex of claim 1 wherein
X is

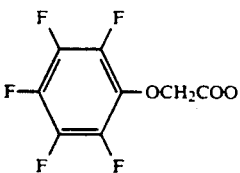

Y is (2S,4S)-4-(Di-m-tolylphosphino)-2-[(di-m-tolyl-phosphino)methyl]-1-(diphenylphosphinoyl)pyr-rolidine, and L is 1,5-Cyclooctadiene.

13. The chiral rhodium-diphosphine complex of claim 1 wherein
X is

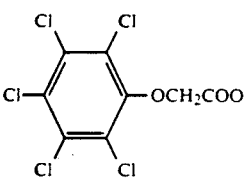

Y is (2S,4S)-4-(Di-m-tolylphosphino)-2-[(di-m-tolyl-phosphino)methyl]-1-(diphenylphosphinoyl)pyr-rolidine, and L is 1,5-Cyclooctadiene.

14. The chiral rhodium-diphosphine complex of claim 1 wherein
X is

CH₃OCH₂COO

Y is (2S,4S)-4-(Di-m-tolylphosphino)-2-[(di-m-tolyl-phosphino)methyl]-1-(diphenylphosphinoyl)pyr-rolidine, and L is 1,5-Cyclooctadiene.

15. The chiral rhodium-diphosphine complex of claim 1 wherein
X is

C₂H₅OCH₂COO

Y is (2S,4S)-4-(Di-m-tolylphosphino)-2-[(di-m-tolyl-phosphino)methyl]-1-(diphenylphosphinoyl)pyr-rolidine, and L is 1,5-Cyclooctadiene.

16. The chiral rhodium-diphosphine complex of claim 1 wherein
X is

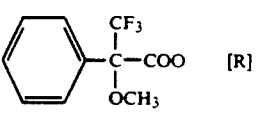

Y is (2S,4S)-4-(Di-m-tolylphosphino)-2-[(di-m-tolyl-phosphino)methyl]-1-(diphenylphosphinoyl)pyr-rolidine, and L is 1,5-Cyclooctadiene.

17. The chiral rhodium-diphosphine complex of claim 1 wherein
X is

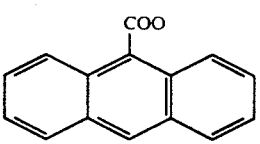

Y is (2S,4S)-4-(Di-m-tolylphosphino)-2-[(di-m-tolyl-phosphino)methyl]-1-(diphenylphosphinoyl)pyr-rolidine, and L is 1,5-Cyclooctadiene.

18. The chiral rhodium-diphosphine complex of claim 1 wherein R' is —OR⁷ and R² and R³ are fluorine.

19. The chiral rhodium-diphosphine complex of claim 1 wherein R' is —OR⁷, R² is trifluoromethyl and R³ is phenyl.

20. The chiral rhodium-diphosphine complex of claim 1 in which R' is phenyl and R² and R³ are fluorine or R² is fluorine and R³ is hydrogen.

21. The chiral rhodium-diphosphine complex of claim 1 wherein the diphosphine ligand is (2S,4S)-4-(di-m-tolylphosphino)-2-[(di-m-tolylphosphino)methyl]-1-(diphenylphosphinoyl)-pyrrolidine.

22. The chiral rhodium-diphosphine complex of claim 1 wherein
X is

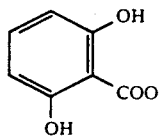

Y is (2S,4S)-4-(Di-m-tolylphosphino)-2-[(di-m-tolyl-phosphino)methyl]-1-(diphenylphosphinoyl)pyr-rolidine, and L is 1,5-Cyclooctadiene.

23. The chiral rhodium-diphosphine complex of claim 1 wherein
X is

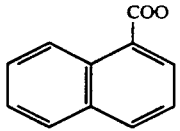

Y is (2S,4S)-4-(Di-m-tolylphosphino)-2-[(di-m-tolyl-phosphino)methyl]-1-(diphenylphosphinoyl)pyr-rolidine, and L is 1,5-Cyclooctadiene.

24. The chiral rhodium-diphosphine complex of claim 1 selected from the group consisting of:
[Rh(C₆F₅-O-CF₂-COO) (2S,4S)-4-(Di-m-tolylphos-phino)-2-[(di-m-tolylphosphino)methyl]-1-(diphenyl-phosphinoyl)pyrrolidine(Lp)]o,
[Rh((R)-C₆H₅-C(CF₃) (OCH₃)-COO) (2S,4S)-4-(Di-m-tolylphosphino)-2-[(di-m-tolylphosphino)methyl]-1-(diphenylphosphinoyl)pyrrolidine(Lp)]o, and
[Rh(C₆H₅-CHF-COO) (2S,4S)-4-(Di-m-tolylphos-phino)-2-[(di-m-tolylphosphino)methyl]-1-(diphenyl-phosphinoyl)pyrrolidine(Lp)]o.

25. The chiral rhodium-diphosphine complex of claim 24 wherein L is 1,5-cyclooctadiene.

26. The chiral rhodium-diphosphine complex of claim 1 wherein
X is

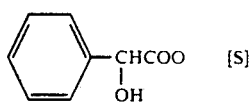

Y is (2S,4S)-4-(Di-m-tolylphosphino)-2-[(di-m-tolylphosphino)methyl]-1-(diphenylphosphinoyl)pyrrolidine, and L is 1,5-Cyclooctadiene.

27. The chiral rhodium-diphosphine complex of claim 1 wherein
X is

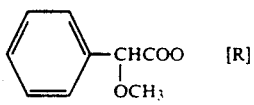

Y is (2S,4S)-4-(Di-m-tolylphosphino)-2-[(di-m-tolylphosphino)methyl]-1-(diphenylphosphinoyl)pyrrolidine, and L is 1,5-Cyclooctadiene.

28. The chiral rhodium-diphosphine complex of claim 1 wherein
X is

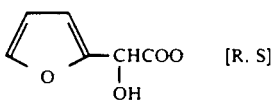

Y is (2S,4S)-4-(Di-m-tolylphosphino)-2-[(di-m-tolylphosphino)methyl]-1-(diphenylphosphinoyl)pyrrolidine, and L is 1,5-Cyclooctadiene.

29. The chiral rhodium-diphosphine complex of claim 1 wherein
X is

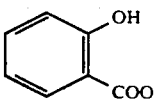

Y is (2S,4S)-4-(Di-m-tolylphosphino)-2-[(di-m-tolylphosphino)methyl]-1-(diphenylphosphinoyl)pyrrolidine, and L is 1,5-Cyclooctadiene.

30. The chiral rhodium-diphosphine complex of claim 1 wherein
X is

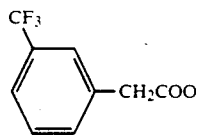

Y is (2S,4S)-4-(Di-m-tolylphosphino)-2-[(di-m-tolylphosphino)methyl]-1-(diphenylphosphinoyl)pyrrolidine, and L is 1,5-Cyclooctadiene.

31. The chiral rhodium-diphosphine complex of claim 1 wherein
X is

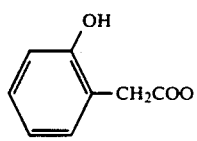

Y is (2S,4S)-4-(Di-m-tolylphosphino)-2-[(di-m-tolylphosphino)methyl]-1-(diphenylphosphinoyl)pyrrolidine, and L is 1,5-Cyclooctadiene.

32. The chiral rhodium-diphosphine complex of claim 1 wherein
X is

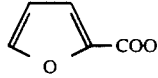

Y is (2S,4S)-4-(Di-m-tolylphosphino)-2-[(di-m-tolylphosphino)methyl]-1-(diphenylphosphinoyl)pyrrolidine, and L is 1,5-Cyclooctadiene.

33. The chiral rhodium-diphosphine complex of claim 1 wherein
X is

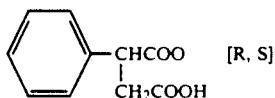

Y is (2S,4S)-4-(Di-m-tolylphosphino)-2-[(di-m-tolylphosphino)methyl]-1-(diphenylphosphinoyl)pyrrolidine, and L is 1,5-Cyclooctadiene.

34. The chiral rhodium-diphosphine complex of claim 1 wherein
X is

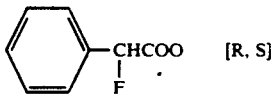

Y is (2S,4S)-4-(Di-m-tolylphosphino)-2-[(di-m-tolylphosphino)methyl]-1-(diphenylphosphinoyl)pyrrolidine or BPPM, and L is 1,5-Cyclooctadiene.

35. The chiral rhodium-diphosphine complex of claim 24 wherein p is 1 and o is 1.

* * * * *

UNITED STATES PATENT AND TRADEMARK OFFICE
CERTIFICATE OF CORRECTION

PATENT NO. : 5,142,063

DATED : August 25, 1992

INVENTOR(S) : BROGER ET AL.

It is certified that error appears in the above-identified patent and that said Letters Patent is hereby corrected as shown below:

Claim 1, Column 12, line 59, delete "methyl[-1" and substitute therefor -- Methyl]-1 --.

Claim 1, Column 12, line 60, delete "(2S,4S)-4(" and substitute therefor -- (2S,4S)-4-( --.

Claim 1, Column 12, line 64, delete "-2[" and substitute therefor -- -2-[ --.

Claim 1, Column 12, line 67, delete "-2[" and substitute therefor -- -2-[ --.

Claim 1, Column 13, line 28, delete "-13."

Claim 1, Column 13, line 29, "COA" should be -- -COA- --.

Column 16:

Claim 18, line 2, delete "R'" and insert therefor -- $R^1$ --.

Claim 19, line 2, delete "R'" and insert therefor -- $R^1$ --.

Claim 20, line 2, delete "R'" and insert therfor -- $R^1$ --.

UNITED STATES PATENT AND TRADEMARK OFFICE
CERTIFICATE OF CORRECTION

PATENT NO. : 5,142,063
DATED : August 25, 1992
INVENTOR(S) : Emil A. Broger

It is certified that error appears in the above-indentified patent and that said Letters Patent is hereby corrected as shown below:

Column 16, claim 24, line 5, delete "$[_o,$" and substitute therefor -- $]_o,$ --.

Signed and Sealed this

First Day of November, 1994

Attest:

BRUCE LEHMAN

Attesting Officer        Commissioner of Patents and Trademarks